US011906691B2

(12) United States Patent
Craddock et al.

(10) Patent No.: US 11,906,691 B2
(45) Date of Patent: Feb. 20, 2024

(54) METHOD FOR IMPROVING NEUTRON INTERPRETATIONS IN SUBSURFACE FORMATIONS

(71) Applicant: SCHLUMBERGER TECHNOLOGY CORPORATION, Sugar Land, TX (US)

(72) Inventors: Paul R. Craddock, Scituate, MA (US); Laurent Mosse, Buenos Aires (AR); Jeffrey R. Miles, Arlington, MA (US); Andrew E. Pomerantz, Lexington, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 17/050,141

(22) PCT Filed: Apr. 22, 2019

(86) PCT No.: PCT/US2019/028563
§ 371 (c)(1),
(2) Date: Oct. 23, 2020

(87) PCT Pub. No.: WO2019/209742
PCT Pub. Date: Oct. 31, 2019

(65) Prior Publication Data
US 2021/0231826 A1    Jul. 29, 2021

Related U.S. Application Data

(60) Provisional application No. 62/661,237, filed on Apr. 23, 2018.

(51) Int. Cl.
*G01V 5/10*      (2006.01)
*E21B 49/00*    (2006.01)
(Continued)

(52) U.S. Cl.
CPC ............... *G01V 5/10* (2013.01); *E21B 49/00* (2013.01); *G01N 21/3563* (2013.01); *G01N 33/241* (2013.01)

(58) Field of Classification Search
CPC ...... G01V 5/10; E21B 49/00; G01N 21/3563; G01N 33/241
See application file for complete search history.

(56) References Cited

U.S. PATENT DOCUMENTS 8,614,573 B2 * 12/2013 Minh .................. G01V 3/18
324/303
8,906,690 B2    12/2014 Pomerantz
(Continued)

FOREIGN PATENT DOCUMENTS

WO    2017083059 A1    5/2017

OTHER PUBLICATIONS

McCleskey et al, Accurate Neutron Porosity Logging in High Temperature Environments, 2017.*
(Continued)

*Primary Examiner* — Mohamed Charioui
*Assistant Examiner* — Lynda Dinh
(74) *Attorney, Agent, or Firm* — Michael L. Flynn

(57) ABSTRACT

Embodiments of the present disclosure are directed towards a method for improving neutron interpretations in a subsurface formation. Embodiments may include estimating mineral concentrations and kerogen concentrations at one or more depths in the subsurface formation and determining kerogen properties at one or more depths in the subsurface formation. Embodiments may further include calculating mineral properties at one or more depths in the subsurface formation and calculating a neutron-based log response to a rock matrix based upon, at least in part, the kerogen prop-
(Continued)

erties and the mineral properties at one or more depths in the subsurface formation by subtracting.

18 Claims, 11 Drawing Sheets

(51) Int. Cl.
G01N 21/35 (2014.01)
G01N 33/24 (2006.01)
G01N 21/3563 (2014.01)

(56) References Cited

U.S. PATENT DOCUMENTS

| | | | |
|---|---|---|---|
| 9,329,122 | B2 | 5/2016 | Herron et al. |
| 10,698,131 | B2 | 6/2020 | Craddock et al. |
| 2012/0312090 | A1* | 12/2012 | Klein ............... G01V 1/50 73/152.05 |
| 2013/0046469 | A1 | 2/2013 | Herron et al. |
| 2013/0269933 | A1 | 10/2013 | Pomerantz et al. |
| 2015/0219782 | A1* | 8/2015 | Kadayam Viswanathan ............... G01N 24/081 324/309 |
| 2016/0003037 | A1* | 1/2016 | Khalid ............... E21B 49/00 73/152.05 |
| 2016/0138392 | A1* | 5/2016 | Pomerantz ............... E21B 25/00 175/50 |
| 2016/0186556 | A1* | 6/2016 | Rasmus ............... G06F 17/11 703/2 |
| 2016/0266275 | A1* | 9/2016 | Akkurt ............... E21B 49/00 |
| 2017/0176639 | A1 | 6/2017 | Mosse et al. |
| 2017/0248011 | A1 | 8/2017 | Craddock et al. |
| 2018/0031732 | A1* | 2/2018 | Mosse ............... G01V 99/005 |

OTHER PUBLICATIONS

Charsky, A.M. and Herron, M.M., 2012, Quantitative analysis of kerogen content and mineralogy in shale cuttings by diffuse reflectance infrared Fourier transform spectroscopy, Paper SCA2012-27, Proceedings of the Society of Core Analysts 2012 International Symposium, Aberdeen, Scotland, Aug. 27-30, 12 pages.

Ellis, D., et al. (1988) Mineral logging parameters: Nuclear and acoustic. The Technical Review, 36(1), 38-52.

Herron, M.M., Herron, S.L. (1996) Quantitative lithology: An application for open and cased hole spectroscopy. SPWLA 37th Annual Logging Symposium. New Orleans, Louisiana. Paper SPWLA-1996-E, 14 pages.

Search Report and Written Opinion of International Patent Application No. PCT/US2019/028563 dated Aug. 12, 2019; 12 pages.

Herron, M.M., et al. (2002) Real-time petrophysical analysis in siliciclastics from the integration or spectroscopy and triple-combo logging, SPE Annual Technical Conference and Exhibition. San Antonio, Texas. Paper SPE-77631, 7 pages.

Herron, M.M., et al. (2014) Kerogen content and maturity, mineralogy and clay typing from DRIFTS analysis of cuttings or core, Petrophysics, 55, 435-446.

Kleinberg, R.L., Vinegar, H.J. (1996) NMR properties of reservoir fluids. The Log Analyst, 37(6), 20-32.

Lis, G.P., et al., 2005, FTIR absorption indices for thermal maturity in comparison with vitrinite reflectance Ro in type-II kerogen from Devonian black shales, Organic Geochemistry, 36, 1533-1552.

Zhou, T., Rose, D., Quinlan, T., Thornton, J., Saldungaray, P., Gerges, N., Noodin, F. and Lukman, A., 2016, Fast neutron cross-section measurement physics and applications, Transactions of the SPWLA 57th Annual Logging Symposium, Jun. 25-29, Reykjavik, Iceland, 19 pages.

Serra, O. (1984) Fundamentals of well-log interpretation. 1. The acquisition of logging data. Developments in Petroleum Science 15A, Elsevier Science Publishers B.V., Amsterdam, pp. 135-149.

Tissot, B., et al. (1978) Geochemical study of the Uinta Basin: formation of petroleum from the Green River formation. Geochimica et Cosmochimica Acta, 42, 1469-1485.

Guidry, K., Luffel, D., Curtis, J., 1995. Development of Laboratory and Petrophysical Techniques for Evaluating Shale Reservoirs, Final Technical Report, No. GRI-95/0496, Refer to Figure 1-5 on p. 56 (306 pages).

McCleskey et al., "Accurate Neutron Porosity Logging in High Temperature Environments", presented at the 58th Annual SPWLA Logging Symposium, Jun. 2017, Oklahoma City, Oklahoma, U.S. A., 7 pages.

Substantive Exam issued in Saudi Arabia Patent Application No. 520420402 dated Aug. 30, 2022, 8 pages with partial English translation.

Substantive Exam issued in Saudi Arabia Patent Application No. 520420402 dated Dec. 28, 2022, 9 pages with English translation.

* cited by examiner

METHOD FOR IMPROVING NEUTRON INTERPRETATIONS IN SUBSURFACE FORMATIONS

CROSS-REFERENCE TO RELATED APPLICATION

This application claims the benefit of U.S. Provisional Application No. 62/661,237, filed on Apr. 23, 2018; the contents of which are incorporated herein by reference.

FIELD

This application relates to methods and apparatus to characterize subterranean formations. Specifically, embodiments described herein use methods to collect, prepare, and analyze formation samples.

BACKGROUND

Neutron-based logs are fundamental and widely used measurements in the petrophysical evaluation of oilfield formations. Neutron-based logs respond principally to the hydrogen content of the formation. A particularly common neutron-based log is a neutron-porosity log, comprising thermal and epithermal neutron measurements, in reference to the dominant energy of the neutrons that are detected. Depending on tool design, both types can have sensitivity to factors such as formation grain density and formation neutron absorption cross section, in addition to the hydrogen concentration of the formation components.

In the petrophysical evaluation of conventional sandstone and carbonate reservoirs, neutron-porosity logs respond predominantly to pore fluids (water and hydrocarbon) in the pore volumes of the rock, as well as to hydroxyls associated to clay minerals, if present. A principal application of this type of neutron logging is to estimate formation porosity comprising the sum volume of pore fluids per unit volume of formation (i.e., a neutron-porosity estimate). Another is to estimate, in combination with a density-porosity estimate, the gas-filled porosity from the so-called 'neutron-density cross-over'.

Another type of neutron-based log is the measurement of the thermal neutron absorption cross section. This quantity is sometimes known as Sigma, and is derived from time-based counting techniques that measure the rate of decay of the neutron population in the formation. These measurements may be based on direct detection of neutrons or on detection of gamma-rays that are induced by the neutrons. Sigma represents the macroscopic thermal neutron absorption cross section of the formation, which is a volumetric sum of the Sigma values for all the formation components, both solid and fluid. The Sigma response of any component is driven by its elemental concentrations, with emphasis on hydrogen, chlorine, and certain other elements with large neutron capture cross sections such as Gd and B which are especially prevalent in clays. The basic principles of neutron-based Sigma logging in conventional formations are well known in the industry.

Yet another type of neutron-based log is the measurement of fast neutron scattering cross sections. One example is the macroscopic cross section for elastic scattering of neutrons with energy near 14.1 MeV, which can be derived from pulsed-neutron tools, and which is known as fast neutron scattering cross section (FNXS). This fast neutron cross section is closely related to the number density of atoms in the formation, which is especially sensitive to gas-filled porosity, but which also varies for different minerals and kerogen types. The total measured macroscopic fast neutron cross section of the formation is a volumetric sum of their individual values for all the formation components, both solid and fluid.

The interpretation of neutron-based logs is challenging in organic-rich mudrocks (commonly termed shale by the oilfield industry). The difficulty arises especially because of the presence of kerogen, which is a hydrogen-rich component that is part of the rock matrix, and which cannot be distinguished from pore fluids by a neutron log. Certain kerogen properties (such as kerogen density, kerogen hydrogen content) are known to range by at least 50% to 100% relative, depending on original depositional setting and level of thermal maturation, and these properties are nearly always unknown without a local calibration, which is rarely available. The response of a neutron-based log to kerogen in shale is rarely known with adequate certainty for an accurate petrophysical evaluation. A method is needed to determine the properties of kerogen in the rock matrix to optimize neutron-based log and neutron-porosity interpretation in shale.

Another challenge in the formation evaluation of shale is their variable and high clay abundance. Clay minerals (illite, smectite, kaolinite, and chlorite) contain inter-layer and structural water. The amount of this water, and therefore hydrogen, differs among the clay minerals. The neutron absorption cross section of clay minerals is similarly variable. It is common to assign fixed clay minerals compositions, assuming only an illite composition. A method is needed to determine an accurate response of neutron-based logs to minerals in the rock matrix.

Neutron-porosity logs respond predominantly to the presence of hydrogen in the formation. The energy loss ("slowing-down") of a neutron occurs predominantly through elastic collisions with hydrogen because the mass of the hydrogen nucleus (a single proton) is very nearly that of a neutron. Neutron-porosity logs are, therefore, measurements of the apparent concentration of hydrogen atoms per unit volume (i.e., the hydrogen density). In practice, it is common for the neutron-porosity response to be scaled in thermal neutron porosity (TNP, p.u.) or hydrogen index (HI) units. Other neutron-based logs may measure thermal neutron absorption cross section (Sigma or $\Sigma$), which can be scaled in capture units (c.u.), or fast neutron scattering cross section (FNXS), which can be scaled in inverse-length (1/m).

For the purposes of describing existing approaches, interpretation of a neutron log is described with respect to one formation property, HI, which is defined as the number of hydrogens per unit volume of material, relative to that of pure water at 75° F. and standard pressure:

$$HI = \frac{\rho \cdot N_H}{0.11 \cdot M_W}, \quad \text{(Eq. 1)}$$

where p is density of the material of interest (i.e., a component of the formation), $N_H$ is number of hydrogens in a molecular unit of the material of interest, and $M_W$ is molecular weight of the molecular unit of the material of interest. The scalar 0.11 is the number of moles of hydrogen in water per unit volume (moles/cm$^3$) at reference conditions. By definition, pure water has a HI value of 1. Hydrocarbons have HI values ranging from that similar to water (e.g., heavy oils) to nearly zero (e.g., low-density gases). In some environments, such as conventional sandstone, limestone, and dolomite reservoirs, the HI of the mineral matrix is nearly (though not exactly) zero. In this case, and with the pore space filled with fresh water, a neutron log is a formation porosity measurement. One relationship between porosity and the (apparent) hydrogen index as measured by the neutron tool, $HI_N$, is $$HI_N = \phi_f HI_f + \Sigma_i \phi_i HI_i \qquad (Eq.\ 2)$$

where $\phi_f$ and $HI_f$ are the volume fraction and hydrogen index of the pore fluid(s), and $\phi_i$ and $HI_i$ are the volume fraction and hydrogen index of mineral(s), i. It follows, therefore, that $$\phi_f = \frac{HI_{ma} - HI_N}{HI_{ma} - HI_f} \qquad (Eq.\ 3)$$

where $HI_{ma}$ is the weighted mineral hydrogen index for the rock matrix, from $\phi_{ma} HI_{ma} = \Sigma_i \phi_i HI_i$, which is close to zero in conventional sandstone and carbonate formations. Analogous relationships can be constructed for neutron-porosity in thermal neutron porosity units, for thermal neutron capture cross section in capture units, and for fast neutron cross section.

SUMMARY

This summary is provided to introduce a selection of concepts that are further described below in the detailed description. This summary is not intended to identify essential features of the claimed subject matter, nor is it intended to be used as an aid in limiting the scope of the claimed subject matter.

In some embodiments, a method (e.g., a computer-implemented method) is executed on a computing device for improving neutron interpretations in a subsurface formation. The method may include estimating mineral concentrations and kerogen concentrations at one or more depths in the subsurface formation and determining kerogen properties at one or more depths in the subsurface formation. The method may further include calculating mineral properties at one or more depths in the subsurface formation and calculating a neutron-based log response to a rock matrix based upon, at least in part, the kerogen properties and the mineral properties at one or more depths in the subsurface formation by subtracting a contribution from the rock matrix from a total neutron response measured by a neutron tool. The matrix components of the formation (kerogen and minerals) are characterized using infrared spectroscopy. The infrared spectroscopy measurement is made on physical samples representing the formation, such as core or cuttings samples. The infrared spectroscopy measurement is made at the surface. The whole formation is characterized using a neutron logging tool. The neutron log is run directly in a borehole traversing an earth formation. In an embodiment, the neutron tool includes at least one neutron source and one or more radiation detectors. The neutron source may be a radioisotope source such as 241AmBe or 252Cf, or it may be an electronic neutron source that can produce pulses of neutrons through deuteron-deuteron (d-D), deuteron-triton (d-T), triton-triton (t-T), or other suitable reactions. The one or more radiation detectors may include neutron detectors using 3He tubes or other types of neutron detectors. The radiation detectors may also include gamma-ray detectors that use scintillator crystals. The count rates from the radiation detectors are combined algorithmically to infer a bulk property of the formation, including but not limited to hydrogen index (HI), thermal neutron porosity, epithermal neutron porosity, thermal neutron absorption cross section (Sigma), or fast-neutron elastic-scattering cross section.

One or more of the following example features may be included. Estimating may be based upon, at least in part, a DRIFTS analysis of at least one sample from the subsurface formation. Determining kerogen properties may include estimating from an infrared spectrum measured by a DRIFTS analysis. The method may include refining the neutron-log response using one or more of nuclear magnetic resonance, resistivity, and dielectric dispersion. Kerogen properties may include one or more of thermal neutron porosity, hydrogen index, macroscopic thermal neutron absorption cross section (Sigma) and/or fast neutron scattering cross section. The method may include performing an interpretation of the neutron-based log response, wherein the interpretation is based upon, at least in part, a standalone porosity. The method may also include performing an interpretation of the neutron-based log response, wherein the interpretation is based upon, at least in part, a volumetric solution using properties of kerogen and minerals. Calculating mineral properties includes a summation of a plurality of individual mineral abundances solved by IR spectroscopy, wherein each of the plurality of individual mineral abundances is multiplied by a respective mineral property. Determining kerogen properties may include estimating from an infrared spectrum measured by an attenuated total reflection or a transmission Fourier transform infrared spectroscopy.

In another example implementation, a computing system for improving neutron interpretations in a subsurface formation is provided. The system may include at least one processor configured to estimate mineral concentrations and kerogen concentrations at one or more depths in the subsurface formation. The at least one processor may be further configured to determine kerogen properties at one or more depths in the subsurface formation and to calculate mineral properties at one or more depths in the subsurface formation. The at least one processor may be further configured to calculate a neutron-based log response of a rock matrix based upon, at least in part, the kerogen properties and the mineral properties at one or more depths in the subsurface formation by subtracting a contribution from the rock matrix from a total neutron response measured by a neutron tool.

One or more of the following example features may be included. Estimating may be based upon, at least in part, a DRIFTS analysis of at least one sample from the subsurface formation. Determining kerogen properties may include estimating from an infrared spectrum measured by a DRIFTS analysis. The one or more processors may be further configured to refine the neutron-log response using one or more of nuclear magnetic resonance, resistivity, and dielectric dispersion. Kerogen properties may include one or more of thermal neutron porosity and hydrogen index, macroscopic thermal neutron absorption cross section (Sigma), and/or fast neutron scattering cross section. The one or more processors may be further configured to perform an interpretation of the neutron-based log response, wherein the interpretation is based upon, at least in part, a standalone porosity. The one or more processors may be further configured to perform an interpretation of the neutron-based log response, wherein the interpretation is based upon, at least in part, a volumetric solution using properties of kerogen and minerals. Calculating mineral properties may include a summation of a plurality of individual mineral abundances solved by IR spectroscopy, wherein each of the plurality of individual mineral abundances is multiplied by a respective mineral property. Determining kerogen properties may include estimating from an infrared spectrum measured by an attenuated total reflection or a transmission Fourier transform infrared spectroscopy.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The discussion below is directed to certain implementations and/or embodiments. It is to be understood that the discussion below may be used for the purpose of enabling a person with ordinary skill in the art to make and use any subject matter defined now or later by the patent "claims" found in any issued patent herein.

It is specifically intended that the claimed combinations of features not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

It will also be understood that, although the terms first, second, etc. may be used herein to describe various elements, these elements should not be limited by these terms. These terms may be used to distinguish one element from another. For example, a first object or step could be termed a second object or step, and, similarly, a second object or step could be termed a first object or step, without departing from the scope of the disclosure. The first object or step, and the second object or step, are both objects or steps, respectively, but they are not to be considered a same object or step.

Figure 1:
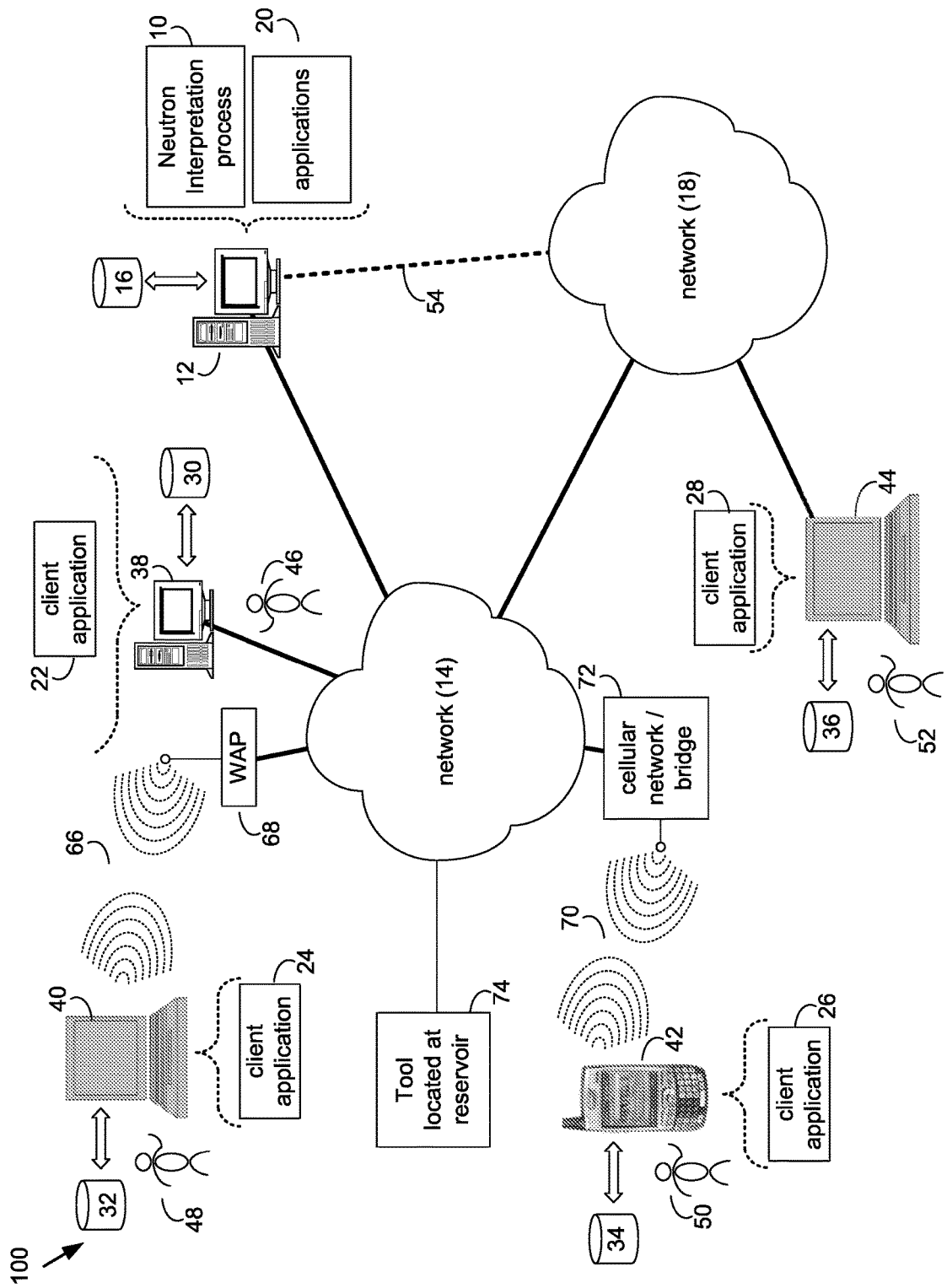
FIG. 1 illustrates a block diagram of a system for a neutron interpretation process in accordance with embodiments of the present disclosure.

Referring to FIG. 1, there is shown a neutron interpretation process 10 that may reside on and may be executed by server computer 12, which may be connected to network 14 (e.g., the Internet or a local area network). Examples of server computer 12 may include, but are not limited to: a personal computer, a server computer, a series of server computers, a mini computer, and a mainframe computer. Server computer 12 may be a web server (or a series of servers) running a network operating system, examples of which may include but are not limited to: Microsoft® Windows® Server; Novell® NetWare®; or Red Hat® Linux®, for example. (Microsoft and Windows are registered trademarks of Microsoft Corporation in the United States, other countries or both; Novell and NetWare are registered trademarks of Novell Corporation in the United States, other countries or both; Red Hat is a registered trademark of Red Hat Corporation in the United States, other countries or both; and Linux is a registered trademark of Linus Torvalds in the United States, other countries or both.) Additionally/alternatively, neutron interpretation process 10 may reside on and be executed, in whole or in part, by a client electronic device, such as a personal computer, notebook computer, or the like.

The instruction sets and subroutines of neutron interpretation process 10, which may include one or more software modules, and which may be stored on storage device 16 coupled to server computer 12, may be executed by one or more processors (not shown) and one or more memory modules (not shown) incorporated into server computer 12. Storage device 16 may include but is not limited to: a hard disk drive; a solid-state drive, a tape drive; an optical drive; a RAID array; a random-access memory (RAM); and a read-only memory (ROM). Storage device 16 may include various types of files and file types.

Server computer 12 may execute a web server application, examples of which may include but are not limited to: Microsoft IIS, Novell Webserver™, or Apache® Webserver, that allows for HTTP (i.e., HyperText Transfer Protocol) access to server computer 12 via network 14 (Webserver is a trademark of Novell Corporation in the United States, other countries, or both; and Apache is a registered trademark of Apache Software Foundation in the United States, other countries, or both). Network 14 may be connected to one or more secondary networks (e.g., network 18), examples of which may include but are not limited to: a local area network; a wide area network; or an intranet, for example.

Neutron interpretation process 10 may be a standalone application or may be an applet/application/script that may interact with and/or be executed within application 20. In addition/as an alternative to being a server-side process, neutron interpretation process 10 may be a client-side process (not shown) that may reside on a client electronic device (described below) and may interact with a client application (e.g., one or more of client applications 22, 24, 26, 28). Further, neutron interpretation process 10 may be a hybrid server-side/client-side process that may interact with application 20 and a client application (e.g., one or more of client applications 22, 24, 26, 28). As such, neutron interpretation process 10 may reside, in whole, or in part, on server computer 12 and/or one or more client electronic devices.

The instruction sets and subroutines of application 20, which may be stored on storage device 16 coupled to server computer 12 may be executed by one or more processors (not shown) and one or more memory modules (not shown) incorporated into server computer 12.

The instruction sets and subroutines of client applications 22, 24, 26, 28, which may be stored on storage devices 30, 32, 34, 36 (respectively) coupled to client electronic devices 38, 40, 42, 44 (respectively), may be executed by one or more processors (not shown) and one or more memory modules (not shown) incorporated into client electronic devices 38, 40, 42, 44 (respectively). Storage devices 30, 32, 34, 36 may include but are not limited to: hard disk drives; solid state drives, tape drives; optical drives; RAID arrays; random access memories (RAM); read-only memories (ROM), compact flash (CF) storage devices, secure digital (SD) storage devices, and a memory stick storage device. Examples of client electronic devices 38, 40, 42, 44 may include, but are not limited to, personal computer 38, laptop computer 40, mobile computing device 42 (such as a smart phone, netbook, or the like), notebook computer 44, for example. Using client applications 22, 24, 26, 28, users 46, 48, 50, 52 may access neutron interpretation process 10.

Users 46, 48, 50, 52 may access neutron interpretation process 10 and/or other applications associated with server computer 12 directly through the device on which the client application (e.g., client applications 22, 24, 26, 28) is executed, namely client electronic devices 38, 40, 42, 44, for example. Users 46, 48, 50, 52 may access process 10 and/or other applications directly through network 14 or through secondary network 18. Further, server computer 12 (i.e., the computer that executes these applications) may be connected to network 14 through secondary network 18, as illustrated with phantom link line 54.

The various client electronic devices may be directly or indirectly coupled to network 14 (or network 18). For example, personal computer 38 is shown directly coupled to network 14 via a hardwired network connection. Further, notebook computer 44 is shown directly coupled to network 18 via a hardwired network connection. Laptop computer 40 is shown wirelessly coupled to network 14 via wireless communication channel 66 established between laptop computer 40 and wireless access point (i.e., WAP) 68, which is shown directly coupled to network 14. WAP 68 may be, for example, an IEEE 802.11a, 802.11b, 802.11g, Wi-Fi, and/or Bluetooth device that is capable of establishing wireless communication channel 66 between laptop computer 40 and WAP 68. Mobile computing device 42 is shown wirelessly coupled to network 14 via wireless communication channel 70 established between mobile computing device 42 and cellular network/bridge 72, which is shown directly coupled to network 14.

As is known in the art, all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. As is known in the art, Bluetooth is a telecommunications industry specification that allows e.g., mobile phones, computers, and personal digital assistants to be interconnected using a short-range wireless connection.

Client electronic devices 38, 40, 42, 44 may each execute an operating system, examples of which may include but are not limited to Microsoft Windows, Microsoft Windows CE®, Red Hat Linux, or other suitable operating system. (Windows CE is a registered trademark of Microsoft Corporation in the United States, other countries, or both).

In some embodiments, neutron interpretation process 10 may generate an output that may be delivered to one or more onsite tools such as reservoir tool 74. Reservoir tool 74 may include, but is not limited to, those available from the Assignee of the present disclosure. In some embodiments, reservoir tool 74 may include one or more processors configured to receive an output from neutron interpretation process 10 and alter the operations of reservoir tool 74.

Embodiments included herein are directed towards a method for using infrared (IR) spectroscopy to estimate kerogen content, clay content, and clay speciation, in addition to the concentrations of other mineral components, in earth samples, such as drill core and drill cuttings.

Figure 2:
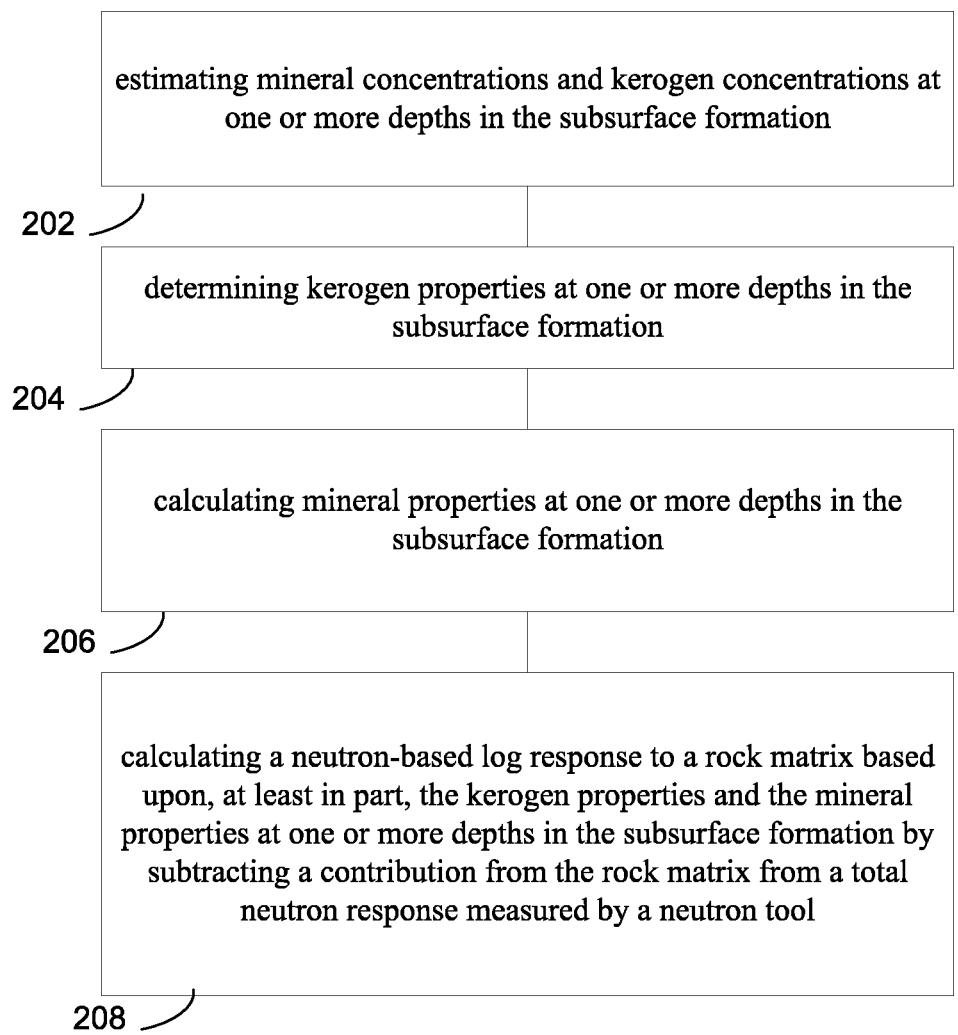
FIG. 2 illustrates a flowchart showing operations consistent with embodiments of the present disclosure.

Referring now to FIG. 2, a flowchart 200 consistent with embodiments of neutron interpretation process 10 is provided. The process may be executed, either in whole, or in part, on a computing device for improving neutron interpretations in a subsurface formation. The method may include estimating (202) mineral concentrations and kerogen concentrations at one or more depths in the subsurface formation and determining (204) kerogen properties at one or more depths in the subsurface formation. The method may further include calculating (206) mineral properties at one or more depths in the subsurface formation and calculating (208) a neutron-based log response to a rock matrix based upon, at least in part, the kerogen properties and the mineral properties at one or more depths in the subsurface formation by subtracting a contribution from the rock matrix from a total neutron response measured by a neutron tool. Numerous other operations are also within the scope of the present disclosure as are discussed in further detail below.

Embodiments of the present disclosure establish a relationship between the IR spectrum 'lineshape' obtained from the analysis of an earth sample containing kerogen as part of the rock matrix and properties of that kerogen to which neutron-based logs respond. This enables the properties of kerogen to be estimated in any unknown formation sample where representative samples of the formation are available. Specific examples of such kerogen properties described include thermal neutron porosity, hydrogen index, macroscopic thermal neutron absorption cross section, fast neutron scattering cross section, and the like. At the same time, the response of neutron-based logs to minerals in the rock matrix may be estimated from the solved mineral concentrations together with their known compositions. When performed on a drill core or drill cuttings, the IR spectroscopy measurement provides a depth 'log' of the neutron response to the rock matrix comprising minerals and kerogen. In some embodiments, the IR data may be obtained using diffuse reflectance infrared Fourier transform spectroscopy, however, the method may be equally applicable to other IR spectroscopy techniques, such as transmission and attenuated total reflection.

Once the neutron response to the rock matrix is known, it may be mathematically subtracted from the total neutron response to the formation, the difference being neutron response to pore fluids. In a basic volumetric interpretation, the information may be used to estimate the formation porosity (i.e., neutron-porosity), though it requires knowledge of the properties of fluid(s) filling the pores. In a more complex volumetric interpretation incorporating additional log measurements, which is described in U.S. Patent Publication No.: 2017/0176639, which is herein incorporated by reference in its entirety, the volume fractions of the individual fluid components of the formation can be determined. In the most complex case, the fluid components in the formation comprise water, hydrocarbon (oil, condensate, or gas), and bitumen; the properties of which are generally known for the relevant formation conditions. A neutron-based log may be interpreted as a standalone measurement, or as one measurement from a plurality of measurements using any suitable mathematical treatments, such as a matrix inversion. Additional petrophysical interpretations of this method not described here are a natural extension to the subject application and will be obvious to those skilled in the art.

In some embodiments, the IR spectrum lineshape interpretation as disclosed herein may be used to determine properties of kerogen that are not necessarily required for neutron-based logs, but are useful for other downhole log measurements. One example is the determination of the hydrogen index which is also beneficial for the interpretation of some nuclear magnetic resonance measurements.

Establishing accurate formation volumes is a key part of petrophysical evaluations of petroleum resources. Existing methods for porosity determinations in organic-rich, low-porosity mudrocks (commonly referred to as shale) are challenging, generally requiring laboratory analysis of intact core.

Accordingly, embodiments included herein are directed towards a new method to enable quantitative interpretation of neutron-based logs (either thermal or epithermal) of subsurface formations in which kerogen (solid, insoluble organic matter) comprises a portion of the solid rock matrix. One expression for the neutron response may be given in hydrogen index units. Another expression for the neutron response may be given in thermal neutron porosity units. Embodiments included herein may be based on novel transforms that quantifies the neutron response to kerogen directly as a function of the kerogen IR signature of a formation sample obtained using IR spectroscopy. The neutron response to kerogen and to formation mineralogy also obtained using IR spectroscopy, may be used together to compute the response of a neutron-based log to the whole rock matrix. Subtracting the matrix contribution from the total formation neutron response can be used to calculate relevant formation volumes, such as pore volume, porosity, or the like. One embodiment of the present disclosure may utilize diffuse reflectance infrared Fourier transform spectroscopy (DRIFTS) to solve for mineral and kerogen content and to estimate kerogen and mineral neutron responses.

Specific example is given to the interpretation of a neutron-porosity log. Beyond neutron-porosity measurements, embodiments of the present disclosure are also relevant for any other neutron-based logs for which porosity or volumetric expressions can be written. Some examples may include, but are not limited to, the macroscopic cross sections for thermal neutron absorption or fast neutron scattering.

In some embodiments, DRIFTS cutting analysis may be available in both vertical and horizontal wells, and in formations with and without kerogen. Embodiments of the present disclosure may be used in all wells irrespectively of the coring program, as the method can be used on cuttings or core samples.

Neutron-based logs are commonly used to interpret formation volumes (e.g., Eq. 2). Most neutron-based logging technologies were developed for interpreting formation volumes in conventional sandstones and carbonate reservoirs, wherein certain neutron responses to the matrix (minerals) is commonly zero or nearly zero.

In organic-rich mudrocks (shales), the matrix properties must be explicitly considered in neutron-based log interpretations (but are rarely so). This is because shales contain both kerogen (solid and insoluble organic matter) and clay minerals and, unlike for conventional reservoirs, the contribution of the matrix to the neutron log response is neither zero, nor can it be approximated as zero. For example, a neutron tool, with respect to hydrogen index, reads as follows in shale (i.e., expanding Eq. 2 for all formation components:

$$HI_N = \phi_w HI_w + \phi_{hc} HI_{hc} + \phi_b HI_b + \Sigma_i \phi_{min,i} HI_{min,i} + \phi_k HI_k \qquad \text{(Eq. 4)}$$

where $\phi_k$ and $HI_k$ are the kerogen volume fraction and the kerogen hydrogen index. Water (w), hydrocarbons (hc), and bitumen (b), if present, are part of the pore volume, whereas minerals (i) and kerogen (k) are part of the rock matrix (ma) volume. Kerogen contains abundant hydrogen, between ~ 3 and 11 wt % depending upon type and level of thermal maturation. Clay minerals contain hydrogen in structural hydroxyls. Kerogen and clay in the matrix have a neutron-porosity log response similar to that of pore fluids, so that neutron porosity reads high in shales (i.e., the neutron log 'sees' hydrogen in kerogen and clays as part of the porosity, not the rock matrix). In cases where kerogen is explicitly included in a neutron log interpretation, the kerogen hydrogen property ($HI_k$, or equivalent) is nearly always not well known or not known at all.

Embodiments included herein describe a method to improve a neutron-based log interpretation in subsurface formations by explicitly accounting for the properties of (i.e., the neutron log response to) kerogen and minerals in the rock matrix.

Embodiments may include a method to quantitatively estimate mineral concentrations (mass or volume fraction) and kerogen concentrations (mass or volume fraction) at every depth in a subsurface formation. Some embodiments may be configured to compute mineralogy and kerogen content from the IR spectrum of a sample using Diffuse Reflectance Infrared Fourier Transform Spectroscopy (DRIFTS) on representative samples of the subsurface formation obtained from drill cuttings or core samples. Additional information on these approaches may be found in U.S. Patent Publication No.: 2013/0046469 and U.S. Pat. No. 8,906,690, which are each incorporated by reference herein in their entirety. Embodiments included herein may be equally applicable to alternatives such as attenuated total reflection or transmission Fourier transform infrared spectroscopy, among others. Further, the IR spectroscopy methods included herein may be used on any other types of earth materials, not limited to drill core or drill cuttings. Downhole logging measurements that provide the same or equivalent mineralogical information are considered further embodiments of this method.

In some embodiments, a method to determine kerogen properties at every depth in a subsurface formation is provided. Accordingly, a kerogen property may be estimated directly from the IR spectrum measured by DRIFTS, using a new method described herein. The IR spectrum of kerogen varies as a function of its composition and structure. IR spectroscopy measurements may respond directly to the type and abundance of molecular bonds (i.e., structure) in the material being studied. Therefore, IR spectroscopy may provide information on certain kerogen properties related to its structure, such as hydrogen properties.

In some embodiments, a method to calculate the mineral properties, individually or in aggregate, at every depth in a subsurface formation is provided. Accordingly, the mineral response may be the summation of the individual mineral abundances solved by IR spectroscopy individually multiplied by their relevant property or another mixing law.

In some embodiments, a method to calculate the neutron-based log response to the rock matrix comprising kerogen and minerals at every depth in a subsurface formation by subtracting the contributions from the rock matrix (minerals and kerogen) from the total neutron response as read by the neutron tool. Optionally, additional log measurements, such as nuclear magnetic resonance, resistivity, dielectric dispersion, or others, can be used to refine the volumetrics derived from the neutron log measurement.

For the purposes of this disclosure, embodiments may consider any subsurface, porous earth formation that may contain a rock matrix comprising inorganic minerals and/or solid, insoluble organic matter (kerogen), with particular reference to organic-rich mudrocks (commonly and herein termed shale).

Embodiments included herein are directed towards a method to optimize a neutron-based log interpretation of a subsurface formation through which a neutron sonde is conveyed, by explicitly solving for the concentrations and relevant properties (e.g., hydrogen index, thermal neutron porosity, macroscopic thermal neutron absorption cross section, fast neutron cross section, etc.) of matrix components in the neutron log measurement. A general output from the interpretation is an estimate of the formation volumes, $$X_{log} = \Sigma_{z=1} \phi_z X_z \quad \text{(Eq. 5)}$$

where $X_{log}$ is the relevant log response to the volumetric summation of all individual formation component z volumes, $\phi_z$, and their relevant property, $X_z$. Eq. 5 can be sufficiently represented as $$X_{log} = \phi_f X_f + \phi_{ma} X_{ma} \quad \text{(Eq. 6)}$$

where subscripts f and ma refer, respectively, to the now-separated volume fractions and properties of the fluids (i.e., porosity) and of the matrix. Solving Eq. 6 with respect to pore volume yields the well-known expression for a matrix-adjusted porosity:

$$\phi_f = \frac{X_{ma} - X_{log}}{X_{ma} - X_f}, \quad \text{(Eq. 7)}$$

For conventional reservoirs without kerogen, $\phi_{ma} X_{ma}$ is the volumetrically-weighted contribution from all minerals in the formation matrix, and can be obviously separated to represent the individual contribution from each mineral. In the case of neutron-porosity logs, Eq. 7 may be expressed as:

$$\phi_f = \frac{TNP_{ma} - TNP_{log}}{TNP_{ma} - TNP_f}, \quad \text{(Eq. 8)}$$

where, one expression for the matrix adjustment accounting for all minerals (i) in the formation is:

$$TNP_{ma} = \sum_i \phi_i TNP_i = \rho_{ma} \sum_i \frac{w_i}{\rho_{g,i}} TNP_i. \quad \text{(Eq. 9)}$$

The interpretation is substantially more challenging in organic-rich mudrocks (shale), principally because of the presence of kerogen that comprises part of the matrix, but also because of potentially complex contributions to the neutron log measurement from minerals and fluids. The matrix adjustment to the neutron-porosity log in shale necessarily becomes, $$TNP_{ma} = \rho_{ma} \left( \sum_i \frac{w_i}{\rho_{g,i}} TNP_i + \frac{w_k}{\rho_k} TNP_k \right), \quad \text{(Eq. 10)}$$

where subscript i and k again refers to mineral and kerogen. Similar expressions of Eqs. 8-10 exist for representing other measured neutron-based responses such as, but not limited to, hydrogen index, thermal neutron capture cross section (Sigma or Y) in capture units, and the fast neutron scattering cross section (FNXS).

Further interpretations may attempt to split the total formation porosity into the fractions of all fluids in the pore volume. In this case, Eq. 6 can be expanded as $$X_{log} = \phi_w X_w + \phi_{ch} X_{hc} + \phi_b X_b + \phi_i X_i + \phi_k X_k, \quad \text{(Eq. 11)}$$

where subscripts w, hc, and b, represent the individual pore components water, light hydrocarbon, and bitumen, respectively. The separation of the total porosity into the relative volume fractions of possible fluids may be performed using a plurality of log measurements, such as including a nuclear magnetic resonance log, a dielectric dispersion log, a resistivity log, a density log, a nuclear spectroscopy log, and the like, or combinations thereof.

A principal barrier to the interpretation of neutron-based logs in shale is a value for a relevant kerogen property ($X_k$, e.g., $TNP_K$, $HI_K$, etc.) and therefore a relevant neutron response to kerogen in the matrix, which are nearly always unknown, and there exists no method to predict these properties at every depth in a formation.

As discussed above, some embodiments of the method described herein may use a diffuse reflectance infrared Fourier transform spectroscopy (DRIFTS) measurement, or an IR spectroscopy measurement more generally, to quantify a property of kerogen (where a property refers to one or more of a plurality of properties), based on a discovered relationship between the lineshape of the IR spectrum associated with kerogen (or a part of the IR spectrum associated with kerogen) and the properties of that kerogen ($X_k$) in a formation sample. Because the same IR spectroscopy measurement can also estimate the mass fraction of kerogen in the formation sample (as discussed in U.S. Patent Publication numbers 2013/0046469, 2017/0248011 and U.S. Pat. No. 8,906,690, which are each incorporated by reference herein in their entirety), the neutron log response to kerogen may be determined. The same IR spectroscopy measurement may further estimate the neutron log response to minerals in the formation sample because the measurement can estimate the mass fractions of minerals in the formation sample and their properties ($X_i$) are either known from the literature or can be computed from existing algorithms developed for formation analysis. The sum of the kerogen k and the mineral i contributions is the matrix contribution in shale, which would otherwise not be determinable or known. Now determined, the matrix contribution can be subtracted from the measured neutron-based log response to the formation (i.e., matrix plus fluids) to obtain an estimate of porosity (e.g., Eq. 7).

In some embodiments, a method to interpret a neutron log in shale may include the following steps, which may be illustrated principally using the measurement of a neutron property, namely hydrogen index, HI and/or thermal neutron porosity, TNP. The HI may be defined as the number of hydrogens per unit volume of material, relative to that of pure water at 75° F. and standard pressure:

$$HI = \frac{\rho \cdot N_H}{0.11 \cdot M_W}, \quad \text{(Eq. 12)}$$

where p is density of the material of interest (i.e., a component of the formation), $N_H$ is number of hydrogens in a molecular unit of the material of interest, and $M_W$ is molecular weight of the molecular unit of the material of interest. The scalar 0.11 is the number of moles of hydrogen in water per unit volume (moles/cm3) at reference conditions.

Embodiments of the present disclosure may include a method for the estimation of mineral and kerogen content. This may include estimating at every depth in a subsurface formation (1) the concentrations (e.g., mass or volume fractions) of inorganic minerals and (2) the concentrations (e.g., mass or volume fractions) of solid organic matter (kerogen) from IR spectroscopy analysis of formation samples. In some embodiments, these concentrations may be estimated using IR spectroscopy on drill cuttings or drill cores recovered from the subsurface formation and prepared appropriately for IR spectroscopic analysis as discussed in U.S. Patent Publication No.: 2013/0046469 and U.S. Pat. No. 8,906,690, which are each incorporated by reference in their entirety. The IR spectrum of a formation sample can be solved for its inorganic mineral and kerogen concentrations as a weighted linear combination of pure standard spectra. Common inorganic minerals in sedimentary rocks for which DRIFTS solves include, but are not limited to, quartz, feldspar, calcite, dolomite, illite, smectite, kaolinite, chlorite, muscovite, anhydrite. The DRIFTS inversion solves for the mass fraction of minerals and kerogen in the formation sample. (It is also possible to convert to volume fractions from the known absolute densities of the mineral and kerogen components of the formation sample.) Mineral densities are known, and kerogen density is known to vary with its composition. Techniques exist to estimate the density of kerogen in a formation sample from the same IR spectroscopy techniques disclosed herein. In some embodiments, the formation sample may be in a preserved state to ensure that the mass fraction is relative to the actual total wet mass, not the mass excluding the fluid that escaped.

Embodiments of the present disclosure may include a method for the estimation of kerogen properties. This may include simultaneously estimating at every depth one or more properties of kerogen ($X_k$) to which a neutron-based log has a response, from the same IR spectroscopy inversion used to estimate mineral and kerogen concentrations. Once the kerogen property and the aforementioned kerogen concentration is known, the neutron log response to kerogen in the rock matrix may be determined.

Figure 3:
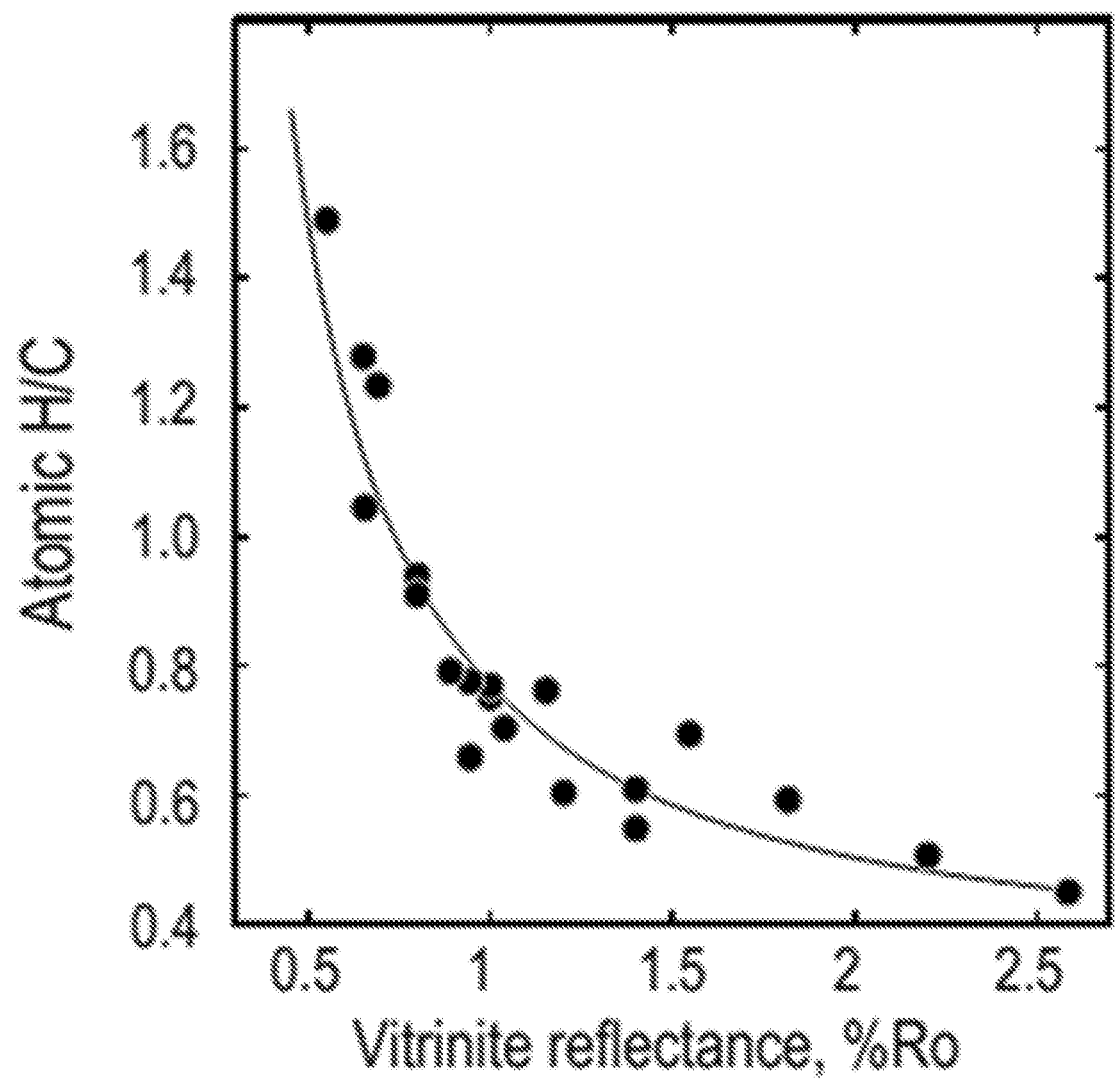
FIG. 3 illustrates a graph depicting atomic hydrogen/carbon ratio of kerogen as a function of thermal maturity (vitrinite reflectance, % Ro)

In some embodiments, the hydrogen index, HI, is exemplified as one property of kerogen. The HI of kerogen is related to its hydrogen content (Eq. 12), and it is known that the hydrogen content of kerogen decreases during thermal maturation by more than a factor of two. FIG. 3 plots the hydrogen concentration of a set of kerogens (expressed as atomic hydrogen/carbon ratio) as a function of their thermal maturity (expressed as vitrinite reflectance, % Ro). The kerogens come from multiple formations, representing global diversity with respect to geography, depositional environment, mineralogy, and thermal maturity. Atomic H/C ratios were obtained directly from elemental analysis of kerogens isolated from formation sample.

It should be noted that these elemental compositions may be determined by laboratory measurements of kerogen isolated from the formation sample after dissolving the minerals using acids. This method may not be practical for the analysis of kerogen properties at every depth in a subsurface formation from drill core or cuttings formation samples. Moreover, this method provides no estimate of kerogen concentration, mineral concentrations, or mineral properties.

Figure 4:
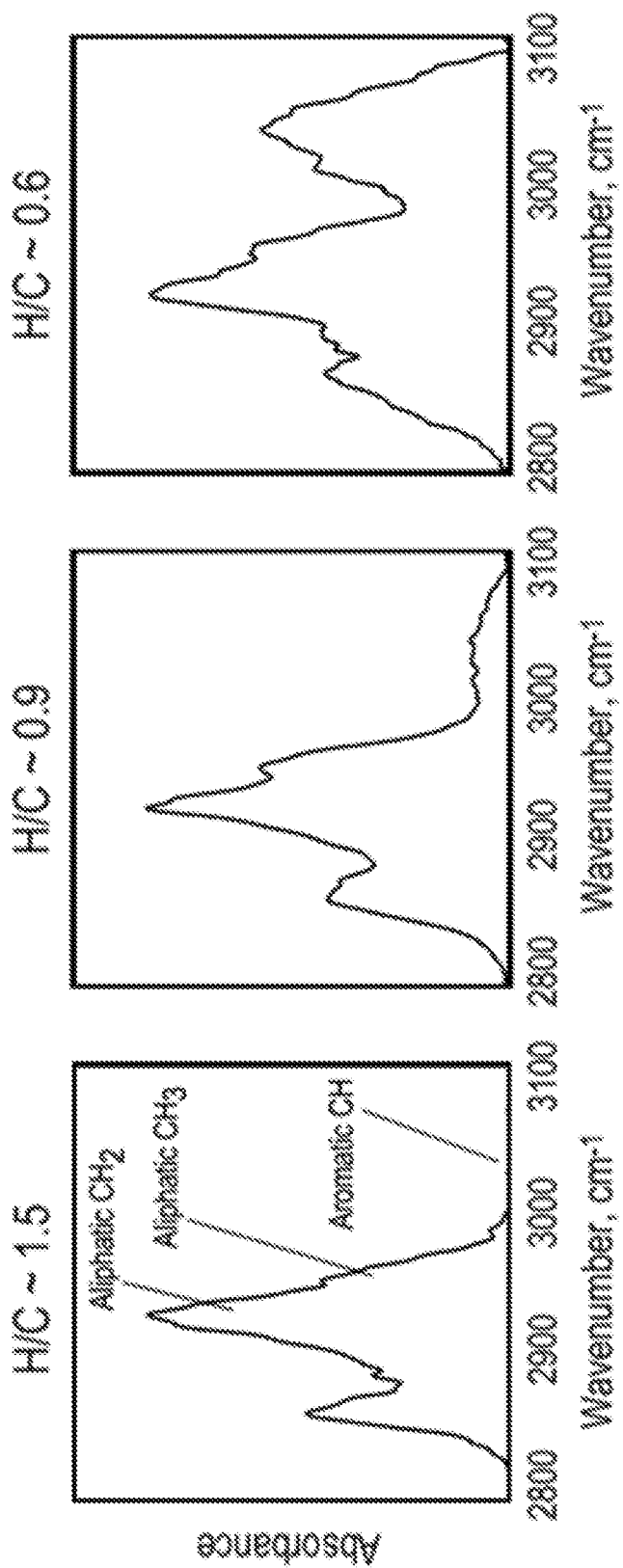
FIG. 4 illustrates a graph depicting a spectrum of three formation samples with magnification of the mid-IR range from 2800-3100 $cm^{-1}$.
Figure 5:
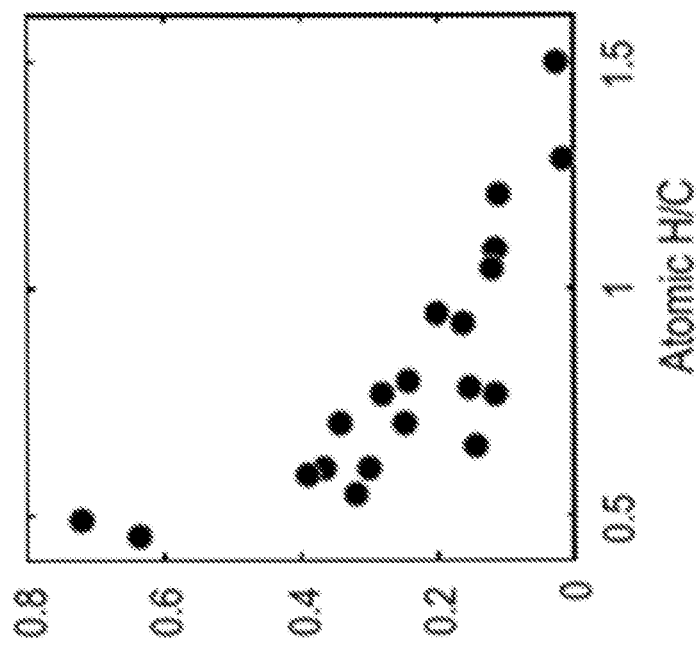
FIG. 5 illustrates graphs depicting correlations between two exemplary IR lineshapes ($CH_3/CH_2$ and $CH/[CH_2+CH_3+CH]$) and atomic H/C ratio of kerogens.
Figure 5:
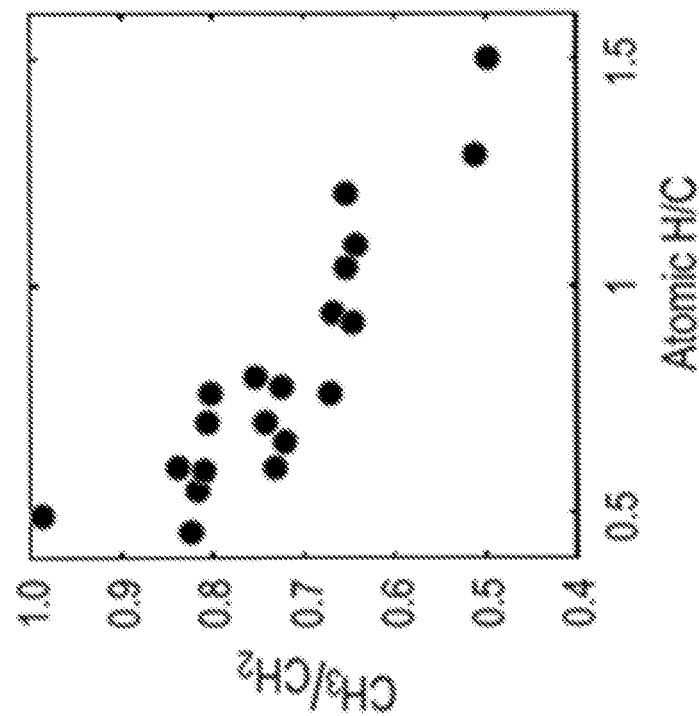

In some embodiments, the property of kerogen may be derived using IR spectroscopy (DRIFTS), wherein the correlation between the lineshape of the IR spectrum (or a part thereof) associated with kerogen and the property of that kerogen is identified. The IR spectrum of kerogen varies as a function of its composition/structure, because the measurement responds directly to the type and abundance of molecular bonds in the material being studied. Therefore, IR spectroscopy may provide information on certain kerogen properties related to its composition/structure. FIG. 4 shows the IR spectra of three formation samples across a region of the IR spectrum between 2800 and 3100 $cm^{-1}$ that may be particularly useful for the interpretation of kerogen composition. FIG. 4 highlights IR bands associated with C—H bonds in kerogen. Also reported at the atomic H/C ratios of the kerogen in the formation samples. The different composition (i.e., H/C ratio) of the kerogens is expressed by their different IR lineshapes. Several IR absorption bands may be recorded in the IR spectra from known vibrational modes in kerogen, including an aliphatic $CH_2$, aliphatic $CH_3$, and aromatic CH stretch. The three sample spectra are rather different because these samples have kerogens of rather different compositions. FIG. 5 illustrates how exemplary ratios of the intensities of these bands correlate systematically with the atomic H/C ratio of kerogen. The IR lineshapes and H/C ratios correlate systematically because both are a direct function of kerogen composition. Any number of fitting laws such as linear, power, exponential, logarithmic, etc., can be used to find the optimal prediction of kerogen H/C ratio from the measured IR spectrum of a formation sample.

Figure 6:
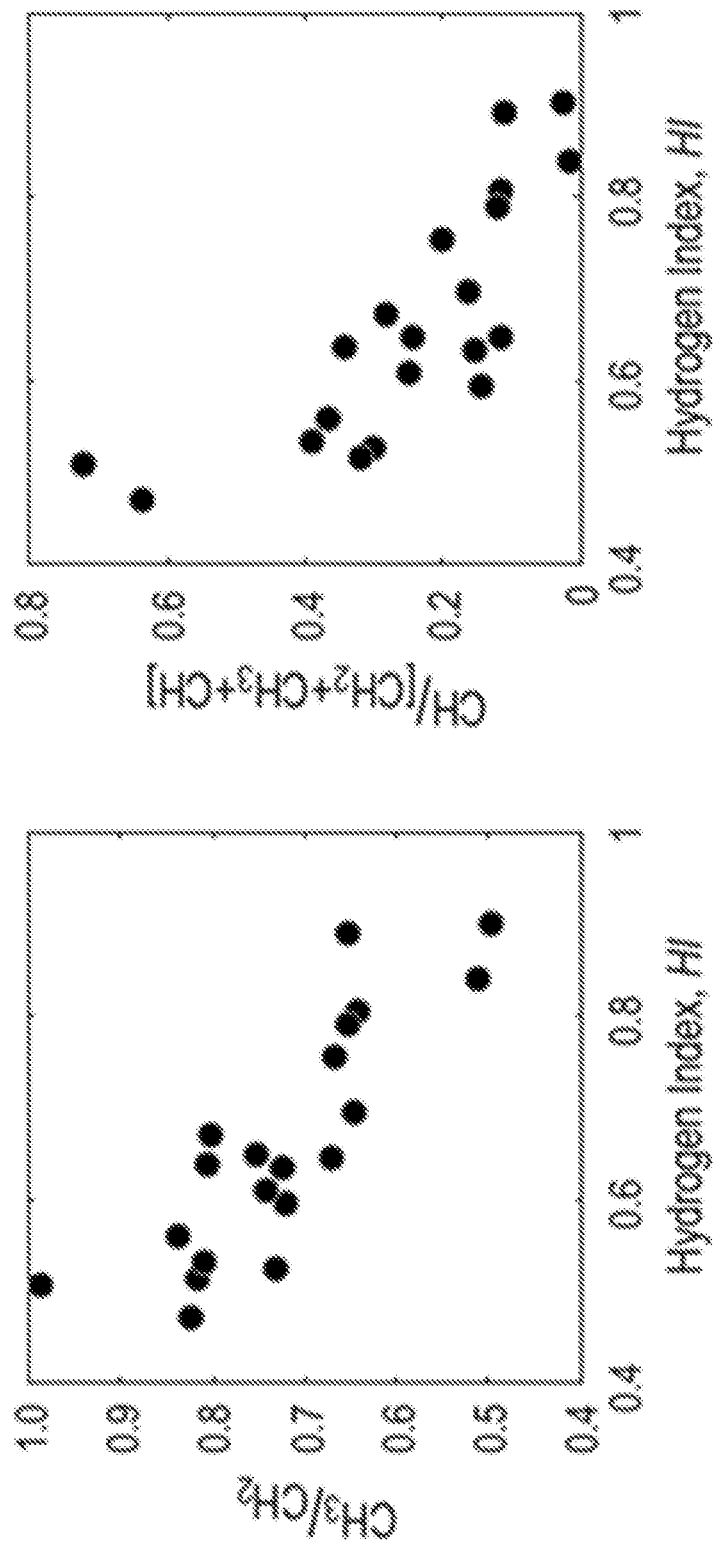
FIG. 6 illustrates graphs depicting correlations between two exemplary IR lineshapes ($CH_3/CH_2$ and $CH/[CH_2+CH_3+CH]$) and hydrogen index, HI, of kerogens.

FIG. 6 illustrates how the same ratios correlate systematically the hydrogen index, $HI_K$, of kerogen. The IR lineshapes and HI correlate systematically because both are direct function of kerogen composition. Any number of fitting laws such as linear, power, exponential, logarithmic, etc., can be used to find the optimal prediction of kerogen HI from the measured IR spectrum of a formation sample.

Figure 7:
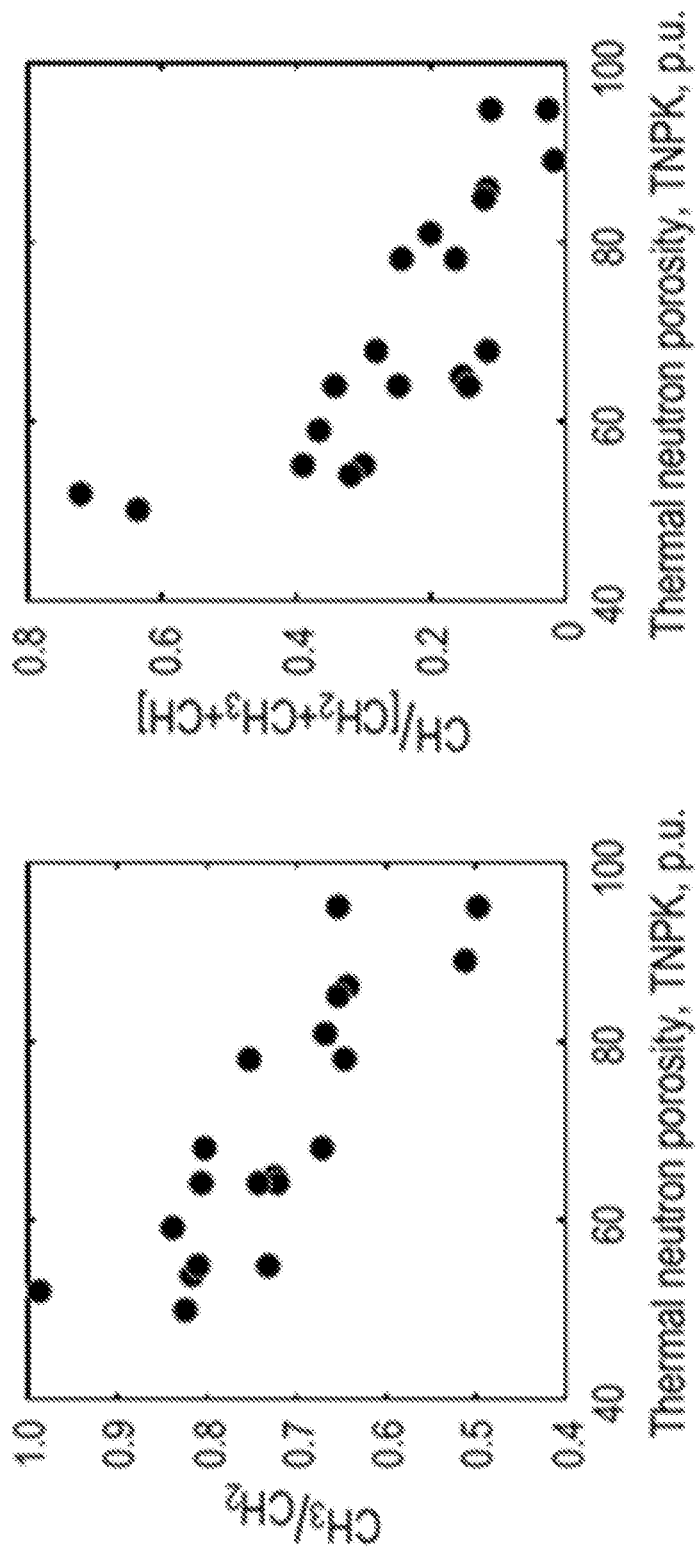
FIG. 7 illustrates graphs depicting correlations between two exemplary IR lineshapes ($CH_3/CH_2$ and $CH/[CH_2+CH_3+CH]$) and thermal neutron porosity, $TNP_k$, of kerogens.

FIG. 7 illustrates how the same ratios correlate systematically with another property of kerogen, namely thermal neutron porosity, $TNP_K$. The IR lineshapes and $TNP_k$ correlate systematically because both are direct functions of kerogen composition. Any number of fitting laws such as linear, power, exponential, logarithmic, etc., can be used to find the optimal prediction of kerogen $TNP_k$ from the measured IR spectrum of a formation sample.

Thus, embodiments included herein have shown that measured IR spectra of formation samples containing kerogen can be diagnostic or predictive of the properties of the kerogen therein to which neutron-based logs are sensitive. Other properties of kerogen not illustrated above to which neutron-based logs are sensitive include, but are not limited to, thermal neutron absorption cross section (Sigma) and fast neutron scattering cross section.

In some embodiments, a ratio of the intensities of two IR bands in the spectral range 2800 to 3100 cm$^{-1}$ associated with kerogen may be used to estimate the property of kerogen. In other embodiments, the ratios of three or more IR bands in the spectral range 2800 to 3100 cm$^{-1}$ associated with kerogen may be used to estimate the property of kerogen.

In some embodiments, the functional form relating the intensities of the IR bands to the property of kerogen is not bounded, and may include a partial-least square regression, a multiple linear regression, a non-linear regression, a non-negativity constraint, or any other known data-fitting procedure.

Figure 8:
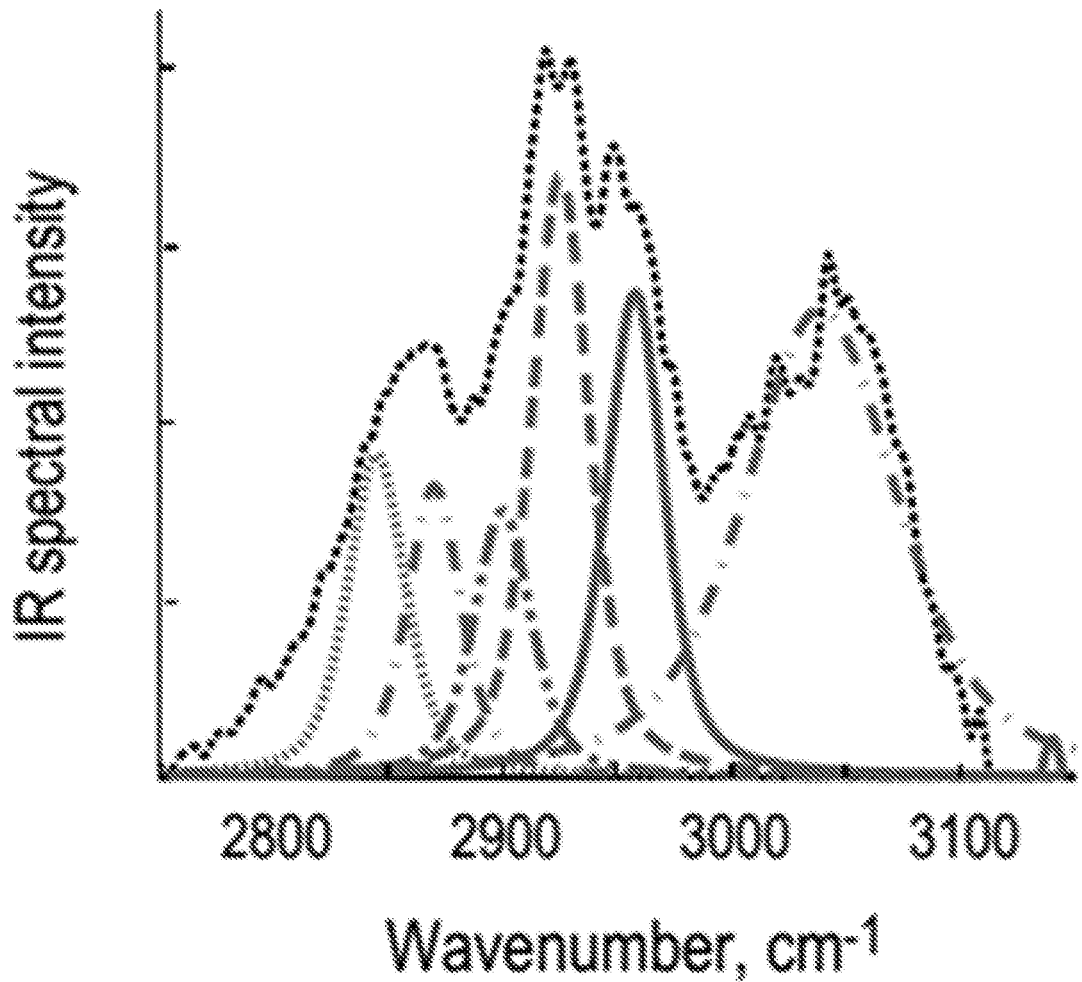
FIG. 8 illustrates an example of a curve-fitting model to interpret the intensities of IR bands in one region of the IR spectra associated kerogen vibrational modes.
Figure 9:
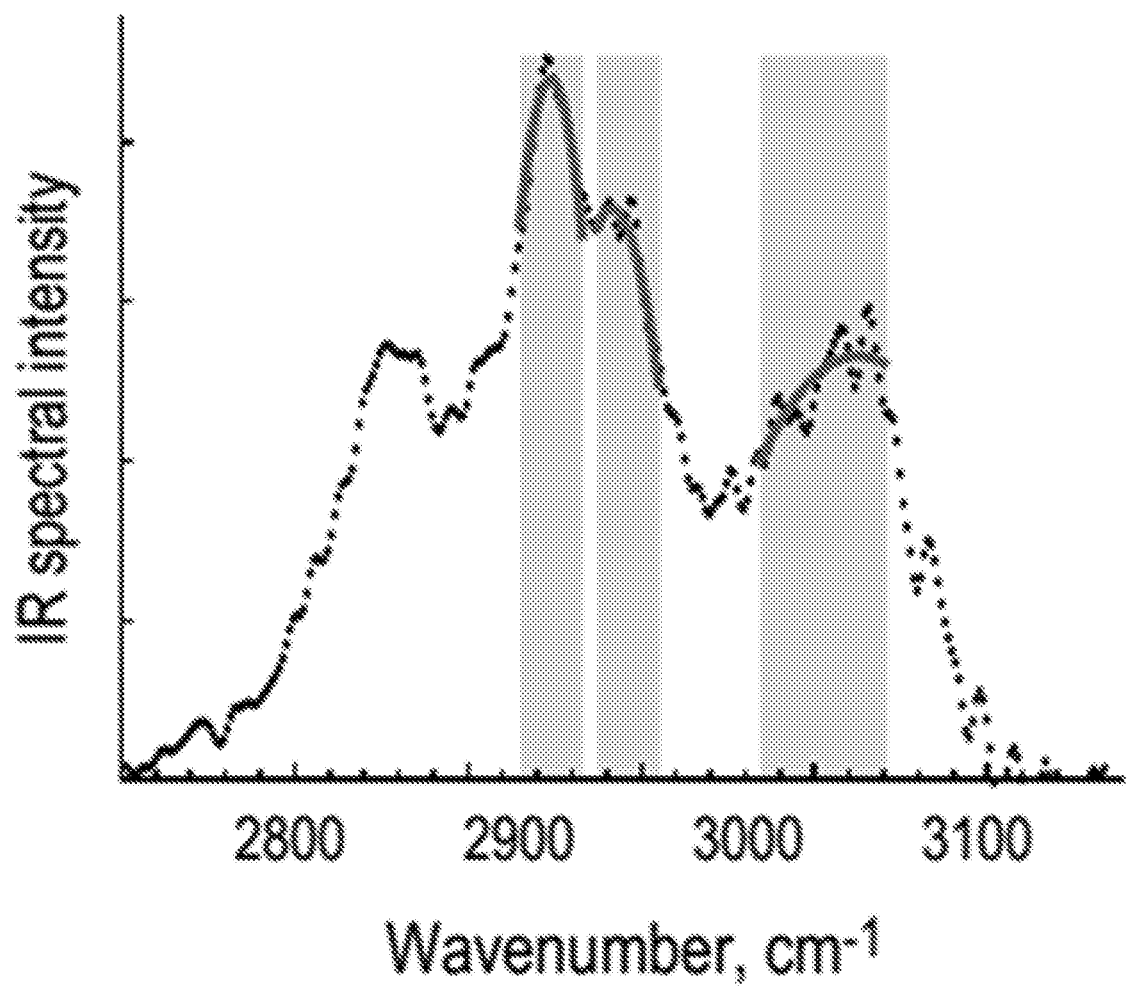
FIG. 9 illustrates an example of a spectral window model to interpret the intensities of IR bands in one region of the IR spectra associated kerogen vibrational modes.

In some embodiments, the IR bands may be identified and quantified by one or more spectral analysis methods, such as Gaussian curve fitting, Lorentzian curve fitting, or any other curve fitting algorithm, or combinations thereof, as illustrated by FIG. 8. In other embodiments, the IR bands may be identified and quantified by defined spectral windows without the need for curve fitting, as illustrated by FIG. 9.

In some embodiments, the IR band intensities may comprise the band maximum, the band full-width at half-maximum, the band half-width at half-maximum, the integrated area under the band, or the like, and may not be limited to the specific embodiments disclosed herein. In some embodiments, one or more band parameters may be derived from the curve fitting procedure. In other embodiments, one or more band parameters may be derived from a fit to the spectrum in the defined spectral window.

In yet other embodiments, the estimates of the band intensities and the resulting kerogen property may include an uncertainty estimate. For example, the value representing the intensity of the vibrational band may be a range of values, such as a distribution function, that represents the 'error' (residuals) of the chosen fitting algorithm to the measured IR spectrum.

Figure 10:
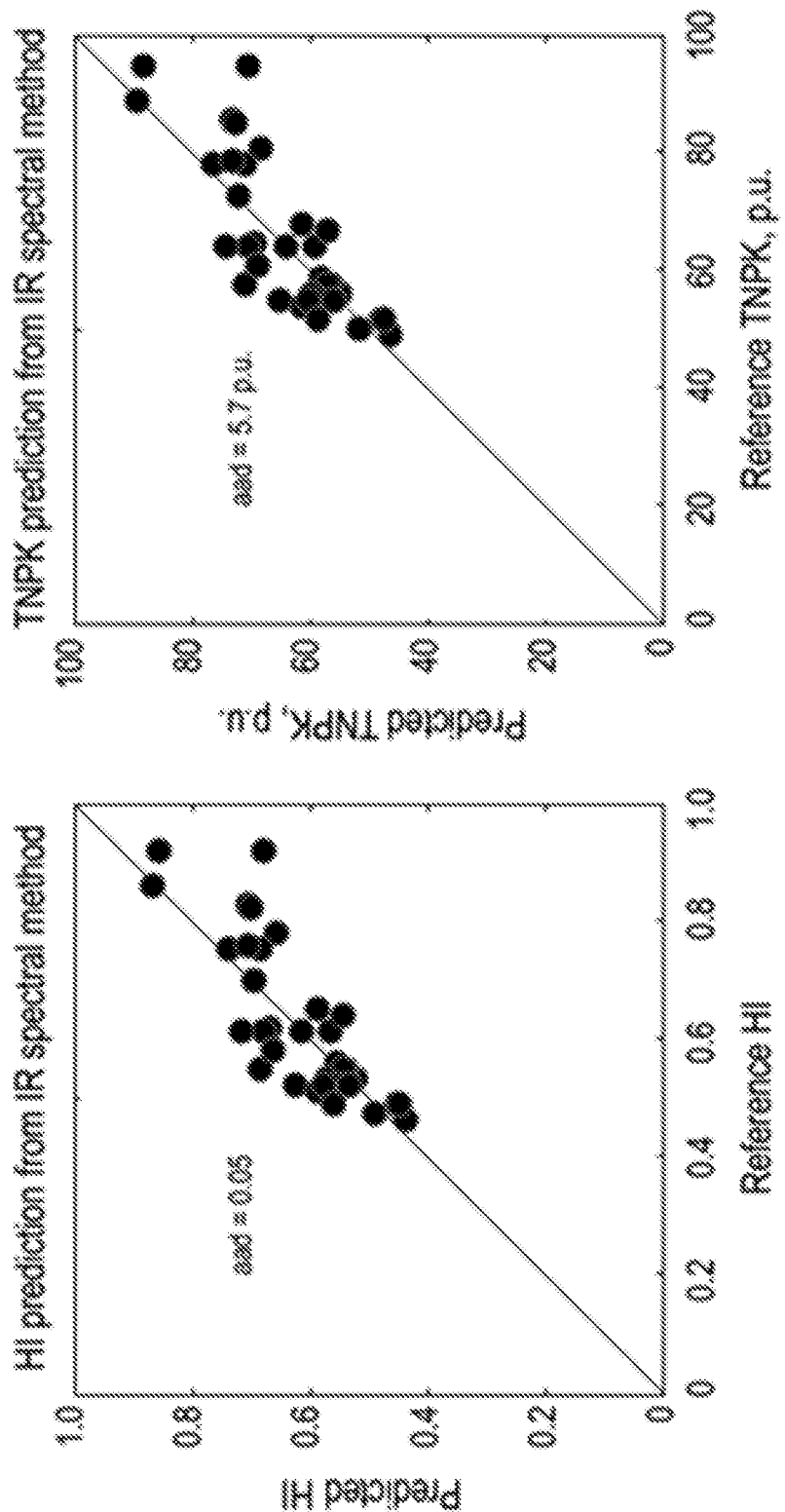
FIG. 10 illustrates graphs showing HI and TNPk values of kerogens in formation samples predicted using IR spectral interpretation methods, plotted against their reference values.

One example of the relationship between the IR lineshape and a property of kerogen, namely HI, is $$HI_k = f(CH_3/CH_2) \tag{Eq. 13}$$

where $CH_3$ and $CH_2$ represent intensities of the aliphatic $CH_3$ and aliphatic $CH_2$ bands, respectively. Another example of the relationship between the IR lineshape and a property of kerogen, namely HI, is $$HI_k = \alpha \cdot CH_2 + \beta \cdot CH_3 + \gamma \cdot CH + \delta \tag{Eq. 14}$$

where $CH_3$, $CH_2$, and $CH$ represent intensities of the aliphatic $CH_3$, aliphatic $CH_2$, and aromatic CH bands, respectively, and $\alpha$, $\beta$, $\gamma$, and $\delta$ are coefficients optimizing the fit of the function. FIG. 10 demonstrates how one embodiment of the IR spectral processing predicts a kerogen property, here the kerogen hydrogen index and the kerogen thermal neutron porosity.

In some embodiments, all other regions of the IR spectrum that express IR absorption bands of kerogen, and all mathematical and other methods to optimize the determination of kerogen properties from one or more of these absorption bands may be utilized.

Embodiments of the present disclosure may include a method for the estimation of mineral properties. The interpretation may include determining the neutron log response to minerals (min) in the rock matrix. The property of the minerals may be property weighted according to the mass or volume fractions of that property summed over all the individual minerals i in the rock matrix, i.e., $$\phi_{min} X_{min} = \Sigma_i \phi_i X_i. \tag{Eq. 15}$$

Expressing Eq. 15 with respect to hydrogen index, HI, yields $$\phi_{min} HI_{min} = \phi_{min} \left( \sum_i \frac{w_i}{\rho_{g,i}} HI_i / \sum_j \frac{w_j}{\rho_{g,j}} \right), \tag{Eq. 16}$$

and with respect to thermal neutron porosity, TNP, yields $$\phi_{min} TNP_{min} = \phi_{min} \left( \sum_i \frac{w_i}{\rho_{g,i}} TNP_i / \sum_j \frac{w_j}{\rho_{g,j}} \right) \tag{Eq. 17}$$

where j is summed over all minerals. Note that in a kerogen-free formation, min and ma are equivalent. $HI_i$, $TNP_i$, and $\rho_{g,i}$ are either known or may be calculated from first principles with knowledge of the composition of mineral i. The hydrogen-bearing clays (e.g., illite, smectite, chlorite, kaolinite) and micas (e.g., muscovite) contributed to the total hydrogen index of the minerals, $HI_{min}$. Other common sedimentary minerals, such as quartz, potassium feldspar, plagioclase, calcite, dolomite, ankerite, siderite, pyrite, and anhydrite, do not contribute substantially to $HI_{min}$. Although this example is illustrated using hydrogen index and thermal neutron porosity as relevant properties, it is also possible to assign mineral values for other properties as previously noted, including, but not limited to, macroscopic neutron absorption cross section, fast neutron scattering cross section, etc.

Figure 11:
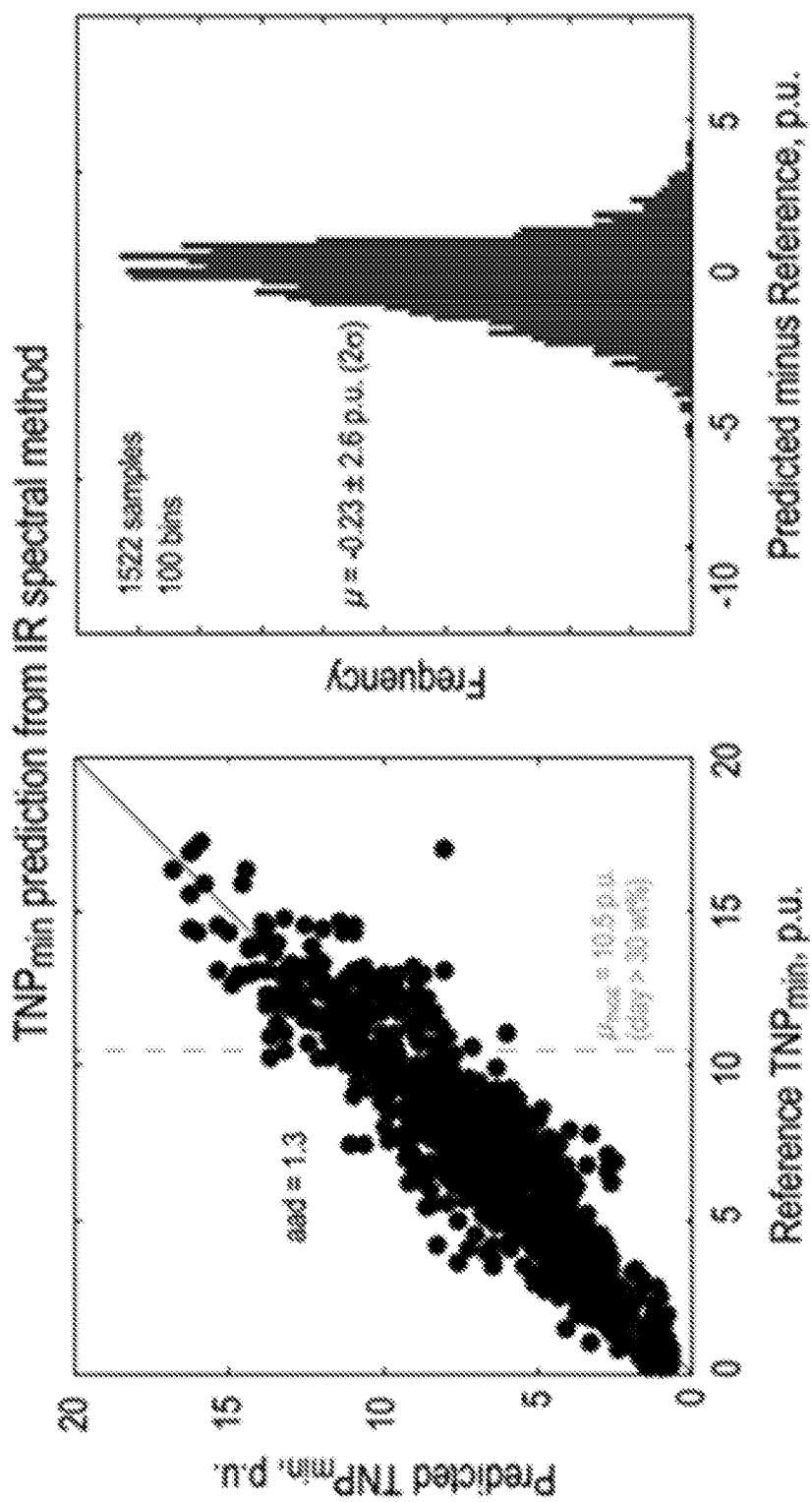
FIG. 11 illustrates graphs showing TNPmin values of the mineral matrix in formation samples predicted using IR spectral interpretation methods, plotted against their reference values.

Alternative methods exist to compute mineral contributions to a neutron log response using bulk elemental concentrations, rather than mineral concentrations as illustrated above. This approach works because the bulk concentrations of elements in a formation sample are governed by its mineralogy. An example of such an approach to correct a neutron-porosity log based on elemental spectroscopy logs is provided below:

$$TNP_{min} = 0.408 - 0.889 \times w_{Si} - 1.014 \times w_{Ca} - 0.257 \times w_{Fe} + 0.675 \times w_S, \tag{Eq. 18}$$

where $TNP_{min}$ is the neutron response to minerals (expressed in thermal neutron porosity units), and w are the mass fractions of the designated elements in the formation sample. FIG. 11 demonstrates that the neutron response to the minerals may be accurately predicted from IR spectroscopy. In this example, the neutron response/property is thermal neutron porosity. The predicted values may be estimated from the bulk elemental concentrations of the formation samples, which may be computed from the sum of the mass fractions of the minerals obtained from the IR spectroscopy measurement described above individually multiplied by their respective bulk elemental compositions.

Embodiments of the present disclosure may include a method for matrix-adjustment of neutron-based logs. The IR spectroscopy measurement performed on subterranean formation samples of known depths may enable a correction (hereafter referred to as a matrix-adjustment) of a neutron-based log measurement of the neutron log response to the matrix of the subterranean formation at the same depths. The matrix may include minerals and/or kerogen, and the IR spectroscopy measurement may account explicitly for one or more neutron properties of both. This matrix-adjustment may be used, for example, to obtain an accurate neutron-porosity estimate in organic-rich mudrocks (shales). The matrix-adjustment (accounting for both minerals and kerogen in the matrix) of a neutron-porosity log was previously described by Eq. 10 for units of thermal neutron porosity:

$$TNP_{ma} = \rho_{ma}\left(\sum_i \frac{w_i}{\rho_{g,i}} TNP_i + \frac{w_k}{\rho_k} TNP_k\right). \quad \text{(Eq. 19)}$$

In some embodiments, the same functional form may be applied to measurements of hydrogen index, thermal neutron absorption cross section (Sigma or $\Sigma$), fast neutron scattering cross section (FNXS), and other relevant properties.

In some embodiments, the porosity estimate may be the more accurate as the bulk properties of the pore components (e.g., $HI_f$, $TNP_f$, $\Sigma_f$, etc.) are more accurately known. The pore volume may be occupied by one or more components. Some components may include, but are not limited to, include bitumen, hydrocarbon, and water. Advanced log interpretations combining multiple log measurements such as, but not limited to, nuclear magnetic resonance, resistivity, dielectric dispersion, may be used to separately quantify the relative volume fractions of the pore components, using any combination of mathematical treatments, such as an inversion as described in U.S. Patent Publication No.: 2017/0176639, which is incorporated by reference herein in its entirety.

In an embodiment, the capabilities of IR spectroscopy are enhanced, and DRIFTS provides the inputs $\phi_k$, $X_k$, $\phi_{min}$, $X_{min}$, where $\phi$ are the concentrations of kerogen and minerals in the matrix, here represented by their volumetric abundances, but which can also be represented by their mass abundances, and X are the properties of kerogen and minerals, which may include, but are not limited to, thermal neutron porosity, hydrogen index, thermal neutron absorption cross section (Sigma), fast neutron scattering cross section. The characterization of the matrix components beneficially improves neutron-based log interpretations in subsurface formations, with particular reference to organic-rich mudrocks (shale).

Embodiments included herein describe a method using an IR spectroscopy measurement to determine one or more properties of kerogen that is required to accurately determine and interpret the response of a neutron-based log to the rock matrix of subsurface formations, wherein the matrix comprises at least one of minerals and kerogen. Certain examples have been presented with respect to determining a thermal neutron porosity and/or a hydrogen index to interpret a neutron-porosity logs. There exist several functions to relate neutron-porosity to neutron tool response, and it is not the purpose of this invention to describe all transformations, as others may be used without departing from the scope of the present disclosure.

In some embodiments, the same IR spectroscopy measurement interpreted as disclosed herein may be used to determine properties of kerogen that are not necessarily required or used for neutron-based logs interpretations, but are useful for other downhole log measurements. One example is the determination of hydrogen index, which may also be beneficial for the interpretation of some nuclear magnetic resonance measurements.

It is specifically intended that the claimed combinations of features not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

It will also be understood that, although the terms first, second, etc. may be used herein to describe various elements, these elements should not be limited by these terms. These terms may be used to distinguish one element from another. For example, a first object or step could be termed a second object or step, and, similarly, a second object or step could be termed a first object or step, without departing from the scope of the disclosure. The first object or step, and the second object or step, are both objects or steps, respectively, but they are not to be considered a same object or step.

The flowchart and block diagrams in the figures illustrate the architecture, functionality, and operation of possible implementations of systems and methods and according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

Although a few example embodiments have been described in detail above, those skilled in the art will readily appreciate that many modifications are possible in the example embodiments without materially departing from the scope of the present disclosure, described herein. Accordingly, such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The invention claimed is:

1. A method for improving neutron interpretations in a subsurface formation comprising:
    deploying a neutron tool directly in a borehole traversing the formation;
    logging the formation using the neutron tool;
    estimating mineral concentrations and kerogen concentrations at one or more depths in the subsurface formation;
    estimating kerogen properties at the one or more depths in the subsurface formation;
    calculating mineral properties at the one or more depths in the subsurface formation by summing a plurality of individual mineral abundances solved by infrared spectroscopy, wherein each of the plurality of individual mineral abundances is multiplied by a respective mineral property;
    calculating a neutron-based log response to a rock matrix based upon, at least in part, the kerogen properties and the mineral properties at the one or more depths in the subsurface formation by subtracting a contribution from the rock matrix associated with the kerogen properties and the mineral properties from a total neutron response measured by the neutron tool when logging the formation; and
    generating and delivering an output to a reservoir tool to alter operation of the reservoir tool, wherein the generated output is based at least in part on an interpretation of the neutron-based log response.

2. The method according to claim 1, wherein estimating the mineral concentrations and the kerogen concentrations is based upon, at least in part, a diffuse reflectance infrared Fourier transform spectroscopy (DRIFTS) analysis of at least one sample from the subsurface formation.

3. The method according to claim 1, wherein estimating the kerogen properties includes estimating from an infrared spectrum measured by a diffuse reflectance infrared Fourier transform spectroscopy (DRIFTS) analysis of at least one sample from the subsurface formation.

4. The method of claim 1, further comprising:
    refining the neutron-based log response using one or more of nuclear magnetic resonance, resistivity and dielectric dispersion.

5. The method of claim 1, wherein at least one of the kerogen properties and the mineral properties include one or more of thermal neutron porosity and hydrogen index.

6. The method of claim 1, wherein at least one of the kerogen properties and the mineral properties include one or more of macroscopic thermal neutron absorption cross section and fast neutron scattering cross section.

7. The method of claim 1, further comprising:
    performing an interpretation of the neutron-based log response, wherein the interpretation is based upon, at least in part, a porosity.

8. The method of claim 1, further comprising:
    performing an interpretation of the neutron-based log response, wherein the interpretation is based upon, at least in part, a volumetric solution using properties of kerogen and minerals.

9. The method according to claim 1, wherein estimating the kerogen properties includes using an infrared spectrum measured by an attenuated total reflection or a transmission Fourier transform infrared spectroscopy.

10. A system for improving neutron interpretations in a subsurface formation comprising:
    a computing system including at least one processor configured to estimate mineral concentrations and kerogen concentrations at one or more depths in the subsurface formation based at least on a formation characterization obtained by utilizing a neutron log obtained by deploying a neutron tool into a borehole traversing the formation, the at least one processor further configured to determine kerogen properties at the one or more depths in the subsurface formation and to calculate mineral properties at the one or more depths in the subsurface formation by summing a plurality of individual mineral abundances solved by infrared spectroscopy, wherein each of the plurality of individual mineral abundances is multiplied by a respective mineral property, the at least one processor further configured to calculate a neutron-based log response to a rock matrix based upon, at least in part, the kerogen properties and the mineral properties at the one or more depths in the subsurface formation by subtracting a contribution from the rock matrix associated with the kerogen properties and the mineral properties from a total neutron response measured by the neutron tool when obtaining the neutron log, and the at least one processor further configured to generate and deliver an output to a reservoir tool to alter operation of the reservoir tool, wherein the generated output is based at least in part on an interpretation of the neutron-based log response.

11. The system according to claim 10, wherein the mineral concentrations and kerogen concentrations are estimated, at least in part, with a diffuse reflectance infrared Fourier transform spectroscopy (DRIFTS) analysis of at least one sample from the subsurface formation.

12. The system according to claim 10, wherein the kerogen properties are estimated, at least in part, from an infrared spectrum measured by a diffuse reflectance infrared Fourier transform spectroscopy (DRIFTS) analysis of at least one sample from the subsurface formation.

13. The system of claim 10, further comprising:
refining the neutron-based log response using one or more of nuclear magnetic resonance, resistivity, and dielectric dispersion.

14. The system of claim 10, wherein at least one of the kerogen properties and the mineral properties include one or more of thermal neutron porosity and hydrogen index.

15. The system of claim 10, wherein at least one of the kerogen properties and the mineral properties include one or more of macroscopic thermal neutron absorption cross section and fast neutron scattering cross section.

16. The system of claim 10, further comprising:
performing an interpretation of the neutron-based log response, wherein the interpretation is based upon, at least in part, a porosity.

17. The system of claim 10, further comprising:
performing an interpretation of the neutron-based log response, wherein the interpretation is based upon, at least in part, a volumetric solution using properties of kerogen and minerals.

18. The system according to claim 10, wherein estimating the kerogen properties includes using an infrared spectrum measured by an attenuated total reflection or a transmission Fourier transform infrared spectroscopy.

\* \* \* \* \*